(12) United States Patent
Sakata et al.

(10) Patent No.: US 9,000,201 B2
(45) Date of Patent: Apr. 7, 2015

(54) ADSORBENT FOR REMOVING METAL COMPOUNDS AND METHOD FOR SAME

(75) Inventors: Yoichi Sakata, Nagoya (JP); Haruto Wakabayashi, Tsukuba (JP); Kazutaka Yanagita, Tsukuba (JP)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 311 days.

(21) Appl. No.: 13/582,700

(22) PCT Filed: Mar. 3, 2011

(86) PCT No.: PCT/IB2011/050920
§ 371 (c)(1),
(2), (4) Date: Nov. 27, 2012

(87) PCT Pub. No.: WO2011/107966
PCT Pub. Date: Sep. 9, 2011

(65) Prior Publication Data
US 2013/0066094 A1    Mar. 14, 2013

Related U.S. Application Data

(60) Provisional application No. 61/311,063, filed on Mar. 5, 2010.

(51) Int. Cl.
*C07F 3/00* (2006.01)
*C07F 3/06* (2006.01)
*C07F 5/00* (2006.01)
*C07F 5/06* (2006.01)

(52) U.S. Cl.
CPC ... *C07F 3/06* (2013.01); *C07F 5/00* (2013.01); *C07F 5/062* (2013.01)

(58) Field of Classification Search
CPC ................................ C07F 3/103; B01J 20/226
USPC .......................................................... 556/118
See application file for complete search history.

(56) References Cited

U.S. PATENT DOCUMENTS 4,797,500 A * 1/1989 Kadokura et al. ............... 556/1
2003/0035763 A1   2/2003 Vergani et al.

FOREIGN PATENT DOCUMENTS

| | | |
|---|---|---|
| JP | 57 159800 | 10/1982 |
| JP | 62 132888 | 6/1987 |
| JP | 62 258388 | 11/1987 |
| JP | 63 39884 | 2/1988 |
| JP | 2 67230 | 3/1990 |
| JP | 5 202067 | 8/1993 |
| JP | 6 41151 | 2/1994 |
| JP | 2003 531150 | 10/2003 |
| JP | 2012 131747 | 7/2012 |
| WO | WO 2008 108085 | 9/2008 |

OTHER PUBLICATIONS

International Search Repot and Written Opinion for corresponding PCT/IB2011/050920, May 31, 2011.

* cited by examiner

*Primary Examiner* — Porfirio Nazario Gonzalez
*Assistant Examiner* — Kofi Adzamli
(74) *Attorney, Agent, or Firm* — Patricia E. McQueeney

(57) ABSTRACT

Disclosed are effective and simple adsorbents and methods of using the adsorbents for removing metal impurities generated during storage, transportation and supply of organometallic compounds. The disclosed adsorbents and methods provide for the easy and effective removal of the metallic impurities or compounds generated from decomposition of the organometallic compound during its transportation, storage, and supply. Namely, the disclosed adsorbents and methods permit the stable supply of a high purity organometallic compound desired in the semiconductor and photovoltaic cell.

10 Claims, 9 Drawing Sheets

ADSORBENT FOR REMOVING METAL COMPOUNDS AND METHOD FOR SAME

CROSS-REFERENCE TO RELATED APPLICATIONS

This application is a 371 of International PCT Application PCT/IB2011/050920, filed Mar. 3, 2011, which claims priority to U.S. provisional application No. 61/311,063, filed Mar. 5, 2010, the entire contents of which are incorporated herein by reference.

BACKGROUND

Organometallic compounds are used as a material for various purposes, such as transparent conductive oxide films for use in fabricating photovoltaic cells and flat panel displays. Many organometallic compounds, such as diethyl zinc (DEZn), easily decompose in the presence of trace moisture, trace oxygen, light, and in some cases heat. In doing so, the organometallic compounds generate metallic compounds. In the case of DEZn, decomposition produces solid Zn and ethane/ethylene which, due to the difference in vapor pressure between ethane/ethylene and DEZn, tends to accumulate in the vapor region and increase the pressure in the storage container. The metallic compound gradually deposits in the storage tank, the supply equipment parts, and the filling lines during storage, transportation, and supply of the organometallic compounds to a manufacturing tool. This becomes problematic because the metallic compound not only contaminates the manufacturing process, but also causes stoppage of parts used in the supply system. Further, the metallic compound may cause further deterioration of the organometallic compounds. In spite of the unstable properties of organometallic compounds, a strong demand remains in the semiconductor and photovoltaic industry to supply these unstable compounds to a manufacturing tool continuously while maintaining high purity.

As a result, purification techniques and supply techniques for organometallic compounds have been developed. JP Pat. No. H6-41151 discloses purification methods for diethyl zinc using column chromatography with activated carbon. JP Pat. No. 2002-3303391 discloses a method for removing impurities from trimethyl indium using sublimation. JP Pat. No. 2001-3217854 discloses a method for purifying a dry organometallic compound by contacting the dry organometallic compound with a copper or nickel catalyst to remove oxygen existing in the dry organometallic compound as an impurity.

However, even if such purification techniques are used, the purification techniques fail to address metallic impurities generated within tanks during storage, transportation, and supply. As a result, it is believed that no effective techniques addressing the stable supply of organometallic compounds have been disclosed to date. More specifically, simple and cost-effective techniques are needed to remove metal impurities generated in tanks and supply equipment during storage, transportation, and supply.

One standard transportation, storage, and supply technique for organometallic compounds is explained with reference to FIG. 1 and FIG. 2. FIG. 1 is a diagram of an exemplary prior art distribution route 100 for supplying organometallic compounds 110 from a production site 120 to a consumption plant 130. The production site 120 may be an overseas production site and the consumption plant 130 may be a domestic consumption plant. A transport tank 140 is filled with an organometallic compound 110 at the production site 120 where the organometallic compound 110 is produced. The transport tank 140 is then transported to a filling plant 150. The transport tank 140 may be transported to the filling plant 150 by a marine transport 160. At the filling plant 150, the organometallic compounds 110 are transferred from the transport tank 140 to one or more storage tanks 170a, 170b, and 170c. Each storage tank 170a, 170b, and 170c is transported to one or more consumers at various consumption plants 180a, 180b, and 180c. The one or more storage tanks 170a, 170b, and 170c may be transported to the consumption plants 180a, 180b, and 180c via a conveyance road.

One problem with the distribution route 100 is that, even if the organometallic compounds are highly purified prior to transport, the compounds will eventually decompose and generate decomposed metallic compounds. Some of these decomposed metallic compounds will diffuse in the organometallic compound and some of the compounds will deposit in the tank and supply equipment during storage and transport. Further, if the organometallic compounds in the transport tank are transported at elevated temperatures (e.g., 60° C.), the amount of decomposed metallic compounds will increase.

FIG. 2 is a diagram of a prior art method 200 for supplying organometallic compounds 110 from a supply tool 210 to a manufacturing tool 220. The storage tank 170 is connected to the supply tool 210 after the storage tank 170 is transported to the consumption plant. The organometallic compounds 110 in the storage tank 170 are then transferred to the supply tank, such as a bubbler 230. The organometallic compounds are then supplied to the manufacturing tool 220 using methods known in the art, for example, a bubbling supply method.

In order to transfer the liquid organometallic compound 110 from the storage tank 170 to the bubbler 230, a carrier gas 234 is introduced into the storage tank 170 through a carrier gas inlet line (not shown) and a carrier gas inlet valve 240 and the storage tank 170 is pressurized. When pressure in the storage tank 170 is increased, the liquid organometallic compound 110 is then transported through the siphon tube 250, and the compound is supplied to the bubbler 230 through a filling valve 260, a first supply pipe 270, a filter 280, and a filling valve 284 filling the bubbler 230 with the liquid organometallic compound 110. This filling system makes it possible to fill both an empty bubbler and a bubbler already containing the organometallic compound after the compound has been used and the volume of the compound in the bubbler decreases.

During supply to the manufacturing tool 220, a carrier gas 282 is introduced into the bubbler 230 through a carrier gas inlet valve 288 and sparger 286, and then the carrier gas 282 is dispersed in the liquid organometallic compound 224 in the bubbler 230. The carrier gas 282 introduced in the bubbler becomes saturated with the organometallic compound 224 and the saturated gas mixture is supplied to the manufacturing tool 220 through a supply valve 290 and a second supply pipe 294.

Deposits on the siphon tube 250, the filling valve 260, the first supply pipe 270, and the filter 280 of the metallic compounds generated due to decomposition of the organometallic compound in the storage tank 170 present several problems for the supply system, making it difficult to supply the organometallic compound to the manufacturing tool stably and continuously. The filter 280 may be easily clogged with the decomposed metallic compounds, requiring frequent repair and corresponding downtime of the supply system. The decomposed metallic compound is generated not only in the storage tank 170 but also in the bubbler 230. During bubbling supply, any decomposed metallic compound in the organometallic compound 224 in the bubbler 230 is scattered together with the gas mixture to the supply valve 290, the second supply pipe 294, and every device attached to the second supply pipe 294, for example, the mass flow controller, the mass flow meter, and any additional filters and valves (not shown in FIG. 2), which may clog these devices. Therefore it is difficult to supply an organometallic compound to a manufacturing tool stably and continuously.

Several techniques have been studied to solve the above problems caused by the decomposed metallic compounds. One technique attempts to reduce the decomposition of the organometallic compound by reducing moisture and oxygen on the surface of the tube and the tank, typically made of stainless steel. Moisture and oxygen are reduced by exposing the stainless steel surface to an electro polish and/or a high purity nitrogen purge process. However since some organometallic compounds only require heat to decompose, the electro polish and nitrogen purge to reduce moisture and oxygen are not a sufficient solution. This solution also takes time and personnel cost.

Another technique uses filtration to reduce the metallic compound. However removing moisture and oxygen on the filter remains difficult and the filters often become clogged with the metallic compound. Thus, these known techniques are not sufficient for reducing metallic compounds generated in organometallic compounds. Recently the demand for these organometallic compounds has increased, so a new solution for the stable supply of these compounds is highly desired by those in the semiconductor field and the photovoltaic field.

SUMMARY

Disclosed are adsorbents for removing a metallic compound from equipment parts used in the photovoltaic or semiconductor industry. The adsorbent is made of metal, wherein the metal has a high adhesion to the metallic compound. The disclosed adsorbents may include one or more of the following aspects:

the equipment parts include storage tanks, transportation tanks, supply equipment tanks, supply lines, and filling lines;

the metal of the metal adsorbent is selected from the group consisting of Li, Be, Na, Mg, Al, K, Ca, Sc, Ti, Cr, Mn, Co, Ni, Zn, Ga, Ge, Rb, Sr, Y, Zr, Nb, Mo, Ru, Rh, Pd, Ag, Cd, In, Sn, Sb, Cs, Ba, Hf, Ta, W, Re, Os, Ir, Pt, Au, Tl, Pb, Bi, Cu, stainless steel, and alloys thereof;

the metallic compound is generated by the decomposition of a liquid organometallic compound;

the liquid organometallic compound is represented by the formula $R_{1-3}$-M where each R of $R_{1-3}$ is independently an alkyl group and M is a metal selected from the group consisting of Li, Be, Na, Mg, Al, K, Ca, Sc, Ti, Cr, Mn, Co, Ni, Zn, Ga, Ge, Rb, Sr, Y, Zr, Nb, Mo, Ru, Rh, Pd, Ag, Cd, In, Sn, Sb, Cs, Ba, Hf, Ta, W, Re, Os, Ir, Pt, Au, Tl, Pb, Bi or compound of these metals;

the liquid organometallic compound is selected from the group consisting of diethyl zinc, dimethyl zinc, triethyl zinc, triethyl aluminum, trimethyl aluminum, trimethyl indium, triethyl indium, trimethyl gallium, or triethyl gallium;

the metallic compounds removed by the metal adsorbent are selected from the group consisting of Li, Be, Na, Mg, Al, K, Ca, Sc, Ti, Cr, Mn, Co, Ni, Zn, Ga, Ge, Rb, Sr, Y, Zr, Nb, Mo, Ru, Rh, Pd, Ag, Cd, In, Sn, Sb, Cs, Ba, Hf, Ta, W, Re, Os, Ir, Pt, Au, Tl, Pb, Bi, oxides thereof, hydroxides thereof, or combinations thereof;

the metal of the metal adsorbent is copper, the metallic compound is zinc generated by the decomposition of diethyl zinc (DEZn);

the shape of the metal adsorbent is selected from a plate, a powder, a wire, a net, and combinations thereof;

the metal adsorbent has at least one flat surface;

the metal adsorbent comprises a copper wire net; and the metal adsorbent is a particulate sponge.

Also disclosed is a method for removing metallic compounds generated from the decomposition of a liquid organometallic compound during the storage, transportation, and supply of the liquid organometallic compound using the adsorbents disclosed herein. The method may include one or more of the following aspects:

contacting a liquid organometallic compound that generates a metallic compound from the decomposition of the liquid organometallic compound with a metal adsorbent made of metal, wherein at least a portion of the metallic compounds is removed from the liquid organometallic compound by the metal adsorbent;

the liquid organometallic compound and metal adsorbent are stored in a tank or tube;

supplying liquid or vapor of the liquid organometallic compound from the tank or tube;

the metal of the metal adsorbent is selected from the group consisting of Li, Be, Na, Mg, Al, K, Ca, Sc, Ti, Cr, Mn, Co, Ni, Zn, Ga, Ge, Rb, Sr, Y, Zr, Nb, Mo, Ru, Rh, Pd, Ag, Cd, In, Sn, Sb, Cs, Ba, Hf, Ta, W, Re, Os, Ir, Pt, Au, Tl, Pb, Bi, Cu, stainless steel, and alloys thereof;

the liquid organometallic compound is represented by the formula $R_{1-3}$-M where each R of $R_{1-3}$ is independently an alkyl group and M is a metal selected from the group consisting of Li, Be, Na, Mg, Al, K, Ca, Sc, Ti, Cr, Mn, Co, Ni, Zn, Ga, Ge, Rb, Sr, Y, Zr, Nb, Mo, Ru, Rh, Pd, Ag, Cd, In, Sn, Sb, Cs, Ba, Hf, Ta, W, Re, Os, Ir, Pt, Au, Tl, Pb, Bi or compounds of these metals;

the liquid organometallic compound is selected from the group consisting of diethyl zinc, dimethyl zinc, triethyl zinc, triethyl aluminum, trimethyl aluminum, trimethyl indium, triethyl indium, trimethyl gallium, triethyl gallium, and combinations thereof;

the metallic compound removed by the metal adsorbent is M, oxides of M, hydroxides of M, or combinations thereof;

the metal of the metal adsorbent is copper, the metallic compound is zinc generated by the decomposition of diethyl zinc (DEZn);

the shape of the metal adsorbent is selected from a plate, a powder, a wire, a net, and combinations thereof;

the metal adsorbent comprises a copper wire net;

exposing the metal adsorbent to pure water;

drying the metal adsorbent to remove the pure water;

exposing the metal adsorbent to a diluted acid solution;

rinsing the metal adsorbent to remove the diluted acid solution from the metal adsorbent;

drying the rinsed metal adsorbent; and storing the liquid organometallic compound and the metal adsorbent in a tank or tube.

Also disclosed is another method for removing a metallic compound generated from the decomposition of a liquid organometallic compound during the storage, transportation, and supply of the liquid organometallic compound using the adsorbents disclosed herein. The method may include one or more of the following aspects:

storing liquid diethyl zinc (DEZn) that generates zinc particles from decomposition of the liquid diethyl zinc in a tank or tube containing an adsorbent made of copper, wherein at least a portion of the zinc particles is removed from the diethyl zinc by the adsorbent made of copper;
the adsorbent made of copper is a copper net;
the copper net has a lattice mesh size of 400 microns by 400 microns;
supplying liquid or vapor of the liquid diethyl zinc from the tank or tube;
exposing the adsorbent made of copper to pure water;
drying the adsorbent made of copper to remove the pure water;
exposing the adsorbent made of copper to a diluted acid solution;
rinsing the adsorbent made of copper to remove the diluted acid solution from the adsorbent;
drying the adsorbent; and
the drying the copper comprises exposing the copper adsorbent to nitrogen gas.

Also disclosed is yet another method for removing metallic compounds generated from the decomposition of a liquid organometallic compound during the storage, transportation, and supply of the liquid organometallic using the adsorbents disclosed herein. The method may include one or more of the following aspects:
exposing the metal adsorbent to pure water;
drying the metal adsorbent to remove the pure water;
exposing the metal adsorbent to a diluted acid solution;
rinsing the metal adsorbent to remove the diluted acid solution from the metal adsorbent;
drying the metal adsorbent;
positioning the metal adsorbent in a storage tank;
filling the storage tank with a liquid organometallic compound;
storing the liquid organometallic compound in the storage tank for a period of time, wherein the metal adsorbent removes at least a portion of a metallic compound generated from the decomposition of the liquid organometallic compound from the liquid organometallic compound;
supplying liquid or vapor of the liquid organometallic compound from the storage tank;
the metal of the metal adsorbent is selected from the group consisting of Li, Be, Na, Mg, Al, K, Ca, Sc, Ti, Cr, Mn, Co, Ni, Zn, Ga, Ge, Rb, Sr, Y, Zr, Nb, Mo, Ru, Rh, Pd, Ag, Cd, In, Sn, Sb, Cs, Ba, Hf, Ta, W, Re, Os, Ir, Pt, Au, Tl, Pb, Bi, Cu, stainless steel, and alloys thereof;
the liquid organometallic compound is selected from the group consisting of diethyl zinc, dimethyl zinc, triethyl zinc, triethyl aluminum, trimethyl aluminum, trimethyl indium, triethyl indium, trimethyl gallium, triethyl gallium, and combinations thereof;
the metal of the metal adsorbent is copper, the metallic compound is zinc generated by the decomposition of diethyl zinc (DEZn); and
the metal adsorbent comprises a copper wire net.

BRIEF DESCRIPTION OF THE DRAWINGS

For a further understanding of the nature and objects of the present invention, reference should be made to the following detailed description, taken in conjunction with the accompanying drawings, in which like elements are given the same or analogous reference numbers and wherein.

DETAILED DESCRIPTION OF PREFERRED EMBODIMENTS

Figure 1:
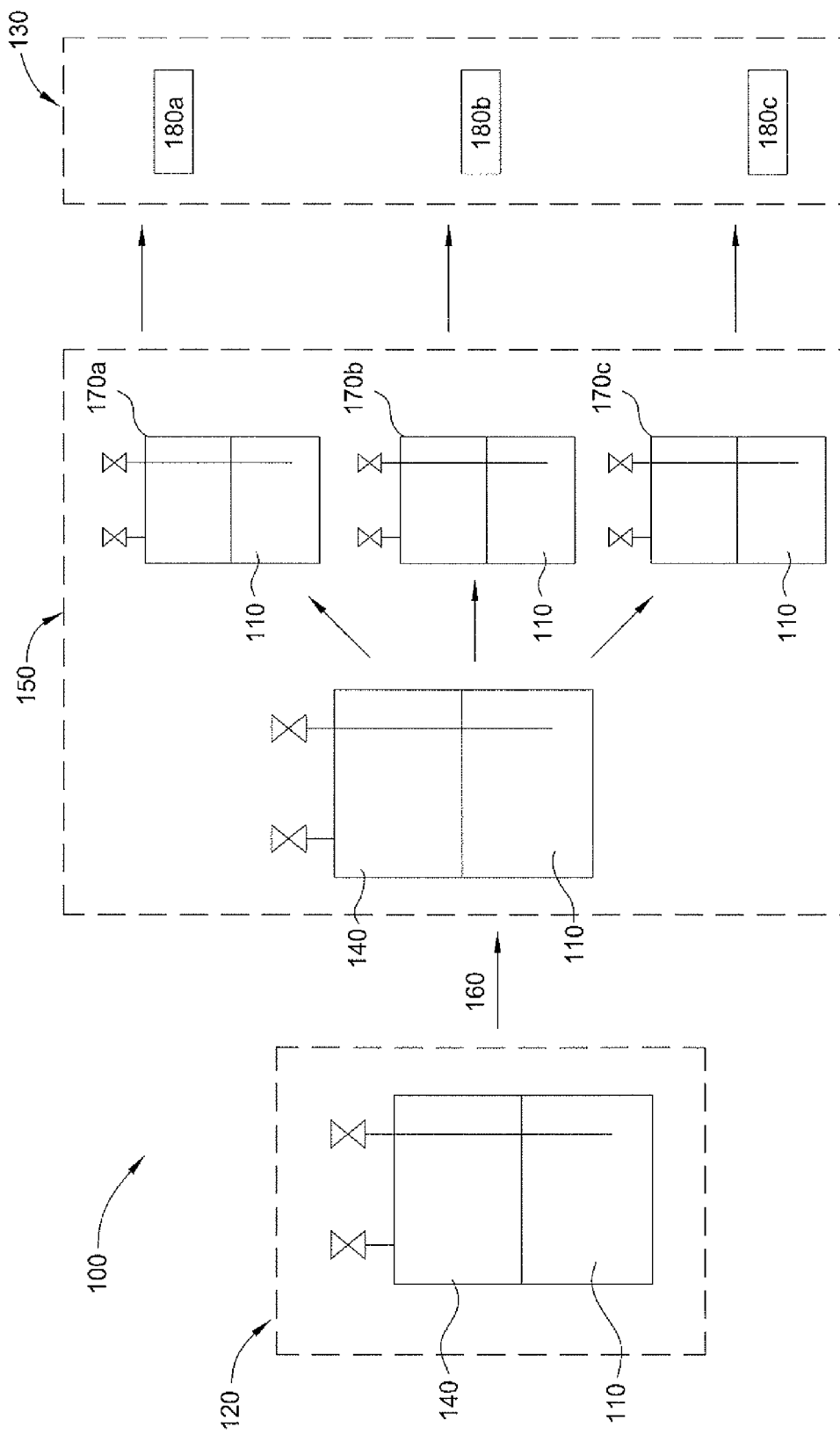
FIG. 1 is a diagram of a prior art distribution route for supplying organometallic compounds from an overseas production site to a domestic customer.
Figure 2:
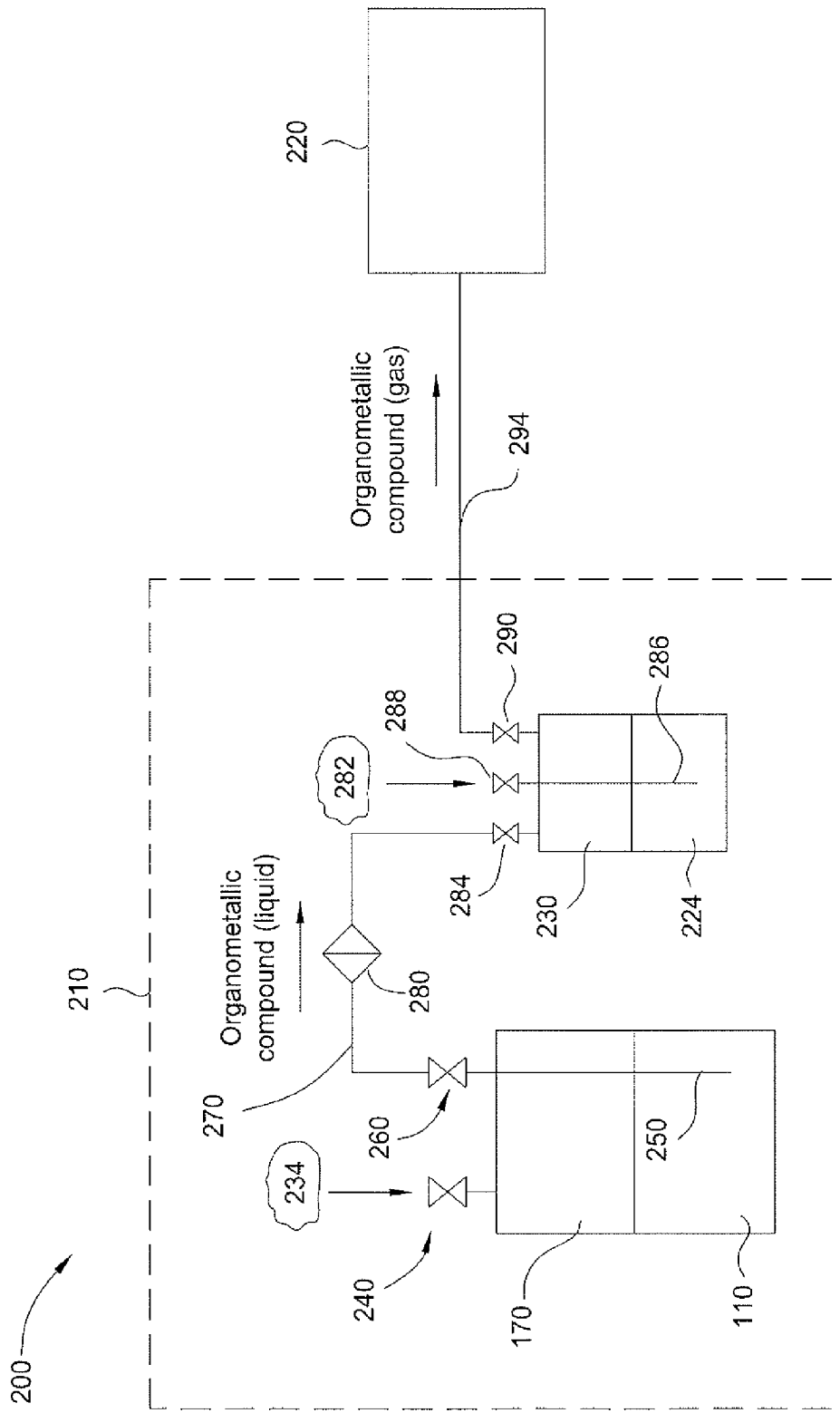
FIG. 2 is a diagram of a prior art method for supplying organometallic compounds to a manufacturing tool.

Disclosed herein are non-limiting embodiments of compositions and methods used in the manufacture of semiconductor, photovoltaic, LCD-TFT, or flat panel type devices.

Disclosed herein are effective and simple adsorbents for removing metal impurities generated during storage, transportation and supply of organometallic compounds. Also disclosed herein are effective and simple methods to remove these metal impurities.

The disclosed adsorbents and methods provide for the easy and effective removal of the metallic impurities or compounds generated from decomposition of the organometallic compound during its transportation, storage, and supply. Namely, the disclosed adsorbents and methods permit the stable supply of a high purity organometallic compound desired in the semiconductor and photovoltaic cell. Specifically, the use of the disclosed adsorbents in the disclosed methods may remove the decomposed metallic compounds generated in the organometallic compound.

As previously discussed, the metallic compounds are generated from the decomposition of organometallic compounds during transportation, storage and supply. Using standard techniques, the metallic compounds could not be removed effectively, so it was difficult to maintain the purity of the organometallic compound during its transportation, storage, and supply. Filtration techniques have been studied as a means for removing the decomposed compound particle. However, filtration techniques were not a fundamental solution because it was necessary to regularly stop the process and change the filter due to clogging. Thanks to the disclosed adsorbents and methods, the following problems plaguing the supply of organometallic compounds in the semiconductor and photovoltaic cell industry may be solved:

The disclosed adsorbents and methods allow for the transportation and storage of the organometallic compound while maintaining its purity by capturing metallic compounds generated during transportation and storage. Also disclosed herein are adsorbents and methods of using the adsorbents that extend equipment life and the time between required maintenance.

Moreover, the adsorbent and methods of using the adsorbent disclosed herein reduce maintenance costs for the supply system that supply the manufacturing tool with organometallic compounds because the decomposed metallic compound deposited on parts of the manufacturing tool is greatly reduced.

The term organometallic compound as used herein refers to compounds which generate metallic compounds by a decomposition reaction and contain $R_{1-3}$-M in its chemical structure where $R_{1-3}$ is one or more alkyl groups and M is a metal. Exemplary metals include Li, Be, Na, Mg, Al, K, Ca, Sc, Ti, Cr, Mn, Co, Ni, Zn, Ga, Ge, Rb, Sr, Y, Zr, Nb, Mo, Ru, Rh, Pd, Ag, Cd, In, Sn, Sb, Cs, Ba, Hf, Ta, W, Re, Os, Ir, Pt, Au, Tl, Pb, Bi or compounds of these metals. Suitable organometallic compounds include diethyl zinc (DEZn), dimethyl zinc, triethyl aluminum, trimethyl aluminum, trimethyl indium, triethyl indium, trimethyl gallium, or triethyl gallium.

The term alkyl group as used herein refers to linear, branched and cyclic alkyls.

The term metallic compound as used herein refers to a metallic compound generated from the decomposition of an organometallic compound. Exemplary metallic compounds may include Zn, Ca, Co, Sr, Fe, Ba, Cu, Mg, V, Cd, Mo, Pb, Ni, Al, Pt, Pd, Mn, Yb, Y, In, Gd, Er, Ga, Sm, Dy, Ce, Tm, Nd, Hf, Ho, La, Lu, Ru, Rh, Ti, Zr, Cr, Ge, Nb, Sn, Sb, Te, Cs, Ta, W, oxides of any of these metals, hydroxides of any of these metals, and mixtures thereof. Suitable metallic compounds include Al, Ga, In, Sn, Zn, Cd, oxides of these metals, hydroxides of these metals, and mixtures thereof.

Adsorbent

The disclosed adsorbents comprise a metallic material capable of adhering to the metallic compound generated by the decomposition of the organometallic compounds.

The disclosed adsorbents are made of metal in contrast to typical adsorbents which are typically made of activated carbon, polymers, or chelating reagents. In contrast to these typical adsorbents, the decomposition of the organometallic compound is not accelerated by the disclosed adsorbents. Further, the adhering ability of the disclosed adsorbents is in contrast to the typical porous adsorbent materials, for example, activated carbon, which physically captures the decomposed metallic compounds via the porosity on the adsorbents surface.

In addition, since the surface of the disclosed adsorbent may be quite flat and exhibits high heat resistance, oxygen and moisture may easily be removed from the disclosed adsorbents before use by nitrogen purge at high temperature. The disclosed adsorbent may be reused many times because this adsorbent is made of metal, so the decomposed compound on this adsorbent can be removed using at least one of a diluted acid solution and pure water.

The adsorbent may be formed from any metallic material capable of adhering to the metallic compound of interest. Exemplary metallic materials may include Li, Be, Na, Mg, Al, K, Ca, Sc, Ti, Cr, Mn, Co, Ni, Zn, Ga, Ge, Rb, Sr, Y, Zr, Nb, Mo, Ru, Rh, Pd, Ag, Cd, In, Sn, Sb, Cs, Ba, Hf, Ta, W, Re, Os, Ir, Pt, Au, Tl, Pb, Bi, Cu, stainless steel, alloys of these metals, and mixtures thereof.

The metal adsorbent may be any shape or form capable of adhering to the metallic compound. The metal adsorbent may be in divided form. Exemplary divided forms include beads, pellets, rings, platelets, granules, cubic shapes, molded geometrically or irregular shapes, sintered materials, wires, nets or any other shape that may be disposed in the interior volume of the storage tanks, supply tanks, or supply tools. The metal adsorbent may be in a monolithic form. Exemplary monolithic forms include blocks, plates, or bricks that may be disposed in the interior volume of the storage tanks, supply tanks, or supply systems. In certain embodiments, at least one surface of the metal adsorbent is a flat surface.

Metal adsorbents having a shape that has a large surface area are preferred. It is believed that metal adsorbents having a larger surface area are more effective in capturing the metal decomposed compound than metal adsorbents having a smaller surface area. In certain embodiments, where a mesh material is used as the metal adsorbent, the surface area may be increased by using a mesh having a smaller lattice mesh size. In certain embodiments, where a mesh material is used as the metal adsorbent, the surface area may be influenced by the packing of the mesh material. For example, a more tightly packed mesh structure may have less surface area than a more loosely packed mesh structure. Metal adsorbents which physically capture the metallic compound are believed to be most effective at adhering with the decomposed metallic compound.

The adsorbent may be in the form of a net comprising metallic wire mesh. The metallic wire mesh may be an S-shaped bent mesh or Dixon packing type mesh. The metallic wire mesh may be a copper wire mesh. In certain embodiments, wire mesh which is used as a demistifier in chemical plants for the separation of mists from gas flow may be used. The size of the lattice mesh of the adsorbent net may be 400 microns by 400 microns. In one embodiment, the adsorbent is an S-shaped mesh made of copper having at least one of the following characteristics: 10 mm packing size, a mesh size number of 50, a surface area of $580 \, m^2/m^3$, an occupied space ratio of 96.5%, and a density/weight of $280 \, kg/m^3$.

Suitable adsorbent nets made of wire mesh are available for TO-TOKU Engineering Corporation of Japan. Suitable adsorbent nets made of copper wire mesh are also available from TO-TOKU Engineering Corporation of Japan under the name Dixon Packing (Cu).

In one exemplary embodiment where the organometallic compound is DEZn, an adsorbent made of copper is most suitable for capturing zinc (e.g., a mixture of zinc, zinc oxide and zinc hydroxide) generated from the thermal decomposition of diethyl zinc (DEZn).

Adsorption Method

The disclosed adsorption methods allow for the storage, transportation and supply of organometallic compounds while maintaining the purity of the organometallic compounds by utilizing the metal adsorbents disclosed above. At a minimum, the disclosed adsorption method involves contacting an organometallic compound that generates metallic compounds from decomposition of the organometallic material with a metal adsorbent made of metal, wherein at least a portion of the metallic compounds is removed by the metal adsorbent. The disclosed metal adsorbent and organometallic compound may be contained within a tank or tube that is used for the transportation, storage, or supply of the organometallic compound during the storage, transportation, or supply of the organometallic compound. The disclosed metal adsorbent may be positioned in the transport tank, storage tank, or supply equipment, prior to, during, or after filling the tank or equipment with the organometallic compound.

Prior to contact with the organometallic compound, the metal adsorbents disclosed herein may be cleaned using at least one of a diluted acid solution and pure water. The metal adsorbent may then be rinsed with pure water or other solvent and then dried. An inert gas, such as nitrogen, argon, helium, or combinations thereof may be used to dry the adsorbent. An endpoint of the drying process may be detected by measuring the moisture content of the inert gas. This process may also be used to clean or regenerate the metal adsorbent after use. It is believed that cleaning the metal adsorbent allows for the metal adsorbent to more effectively capture the metallic compound and maintain the purity of the organometallic compound.

Prior to filling the tank or supply equipment with the organometallic compound, the tank or supply equipment may be exposed to a vacuum or purge process for an extended period of time to remove trace moisture and oxygen from the surface of the tank or supply equipment.

Exemplary Adsorption Method for Transport Tank

Figure 3:
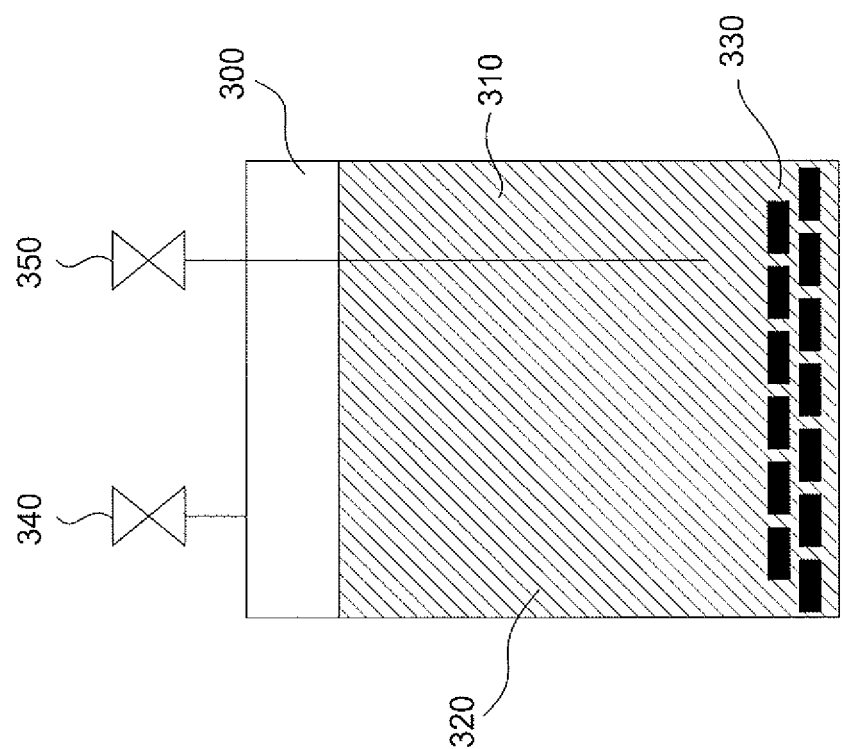
FIG. 3 is a diagram of one embodiment of a transportation tank for transporting an organometallic compound containing a metal adsorbent according to embodiments described herein.

One embodiment of a method for adsorbing the metal decomposed compound generated in a transport tank during transportation and storage of an organometallic compound in a transport tank is explained with reference to FIG. 3. FIG. 3 is a diagram of one embodiment of a transport tank 300 containing a metal adsorbent 330 according to embodiments described herein. The transport tank 300 may include a carrier gas inlet valve 340 for introducing a carrier gas into the transport tank 300 and a filling valve 350 for transferring the organometallic compound from the transport tank 300.

The transport tank 300 is filled with an organometallic compound 310. The transport tank 300 may be filled at a production plant where the organometallic compound 310 is produced. The transport tank 300 may be transported from the production site directly to a consumption site. Similar to the distribution route shown in FIG. 1, the transport tank 300 may be transported from the production site to a filling plant where the organometallic compound 310 is transferred into one or more storage tanks which are transported to the consumption site.

A metal adsorbent 330 as disclosed herein may be positioned within the transport tank 300 prior to, during, or after filling the transport tank with the organometallic compound 310. In certain embodiments, the transport tank 300 may be transported overseas from the production site to the consumption site. The transport tank 300 depicted in FIG. 3 is exemplary and any type of tank capable of storing organometallic compounds may be used. The metallic compound 320 generated in the transport tank 310 during transportation or storage may be adsorbed by the metal adsorbent 330 of this invention without forming a suspension in the transport tank 310.

The metal adsorbent 330 may be cleaned with pure water and then dried using an inert gas as described above. The metal adsorbent 330 may be cleaned with a diluted acid solution, rinsed with water and then dried using an inert gas as described above.

Exemplary Adsorption Method for Storage Tank

Figure 4:
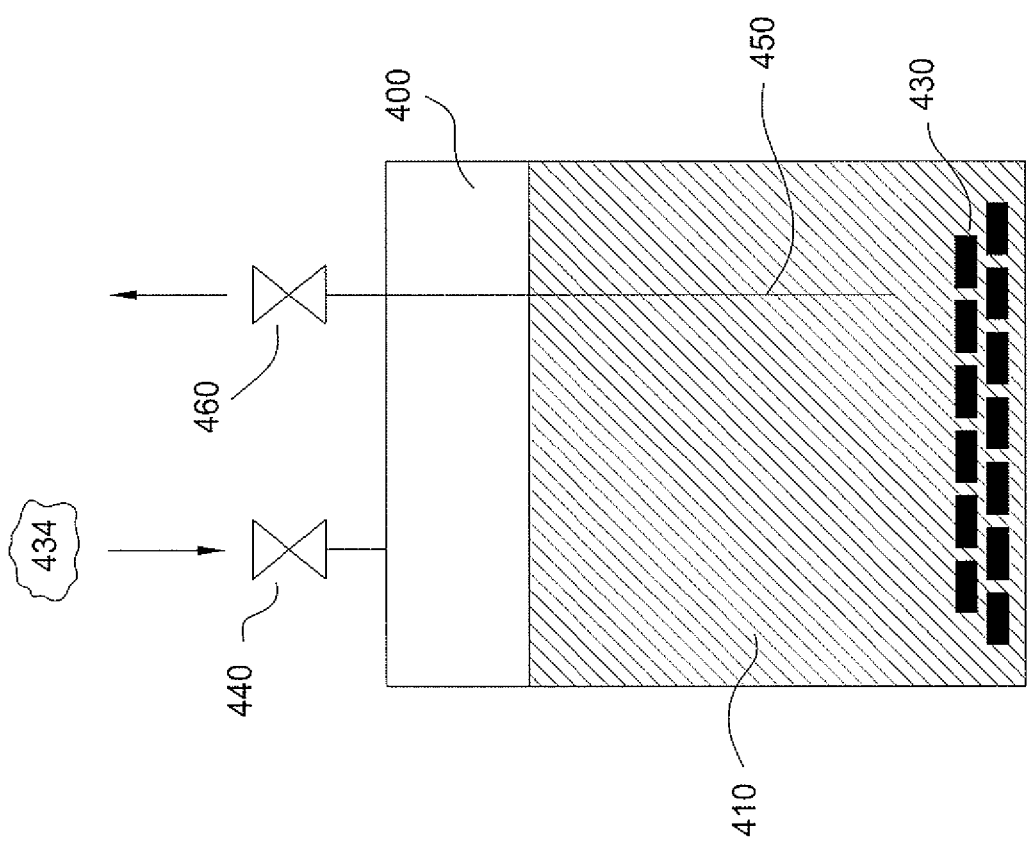
FIG. 4 is a diagram of one embodiment of a storage tank for storing an organometallic compound containing a metal adsorbent according to embodiments described herein.

FIG. 4 is a diagram of one embodiment of a storage tank 400 containing a metal adsorbent 430 according to embodiments described herein. The storage tank 400 may be used for transportation, storage, and supply of liquid organometallic compounds. The storage tank 400 may be filled with an organometallic compound 410 at a filling plant (not shown), and the storage tank 400 is may be transported to a consumption plant (not shown). The storage tank 400 may then be connected with an organometallic supply tool (not shown) for transferring the liquid organometallic compound 410 in the transport tank is supplied to a manufacturing tool.

One exemplary method for supplying the liquid organometallic compound to a manufacturing tool will be explained with reference to FIG. 4. Referring to FIG. 4, a carrier gas 434, for example, argon gas is introduced into the storage tank 400 through a carrier gas inlet valve 440 to pressurize the storage tank 400. When the pressure in the storage tank 400 is increased, the liquid organometallic compound 410 is then transported through the siphon tube 450 and supplied through a filling valve 460 to a supply tool.

In the previously described prior art methods, the metallic compound generated in the storage tank during transportation or storage of the organometallic compound is supplied together with the organometallic compound. The metallic compound suspended in the organometallic compound may deposit on the tube and parts of the supply system (not shown in FIG. 4), for example, valves, flow controllers, vaporizers, gas flow controllers and filters, positioned downstream from the storage tank. As metal decomposed compounds accumulate on the parts, the parts may malfunction or stop leading to downtime for the system so the parts may be removed and either cleaned or replaced.

Referring to FIG. 4, the metallic compound generated by decomposition of the liquid organometallic compound 410 in the storage tank 400 during the transportation, storage or supply of the liquid organometallic compound may be captured by the metal adsorbent 430 disclosed herein if the metal adsorbent 430 described herein is positioned in the storage tank 400. As a result, the organometallic compound 410 which is substantially free of the metallic compound may be supplied through the siphon tube 450.

After or prior to use, the metal adsorbent 430 may be cleaned using a cleaning solution comprising at least one of a diluted acid solution and pure water. The metal adsorbent 430 may be dried by exposing the metal adsorbent to an inert gas purge to remove moisture and oxygen from the metal adsorbent 430. The inert gas purge may be performed at an elevated temperature. The inert gas purge may be performed prior to introducing the metal adsorbent 430 into the storage tank 400 or after removal of the metal adsorbent 430 from the storage tank 400 in order to regenerate the metal adsorbent 430. In one embodiment, the metal adsorbent 430 is exposed to nitrogen gas at an elevated temperature before the metal adsorbent 430 is introduced into the storage tank 400. After cleaning and drying, the metal adsorbent 430 is more effective at capturing the metallic compound and maintaining the purity of the organometallic compound during the transportation, storage or supply of the organometallic compound 410. It should be understood that this method of removing metallic compounds from the liquid organometallic compound 410 in the storage tank 400 and to supply high purity organometallic compound is exemplary, and the methods of using the metal adsorbent described herein are applicable to any situation where it is desirable to maintain the purity of an organometallic compound.

Exemplary Adsorption Method for Bubbler

Figure 5:
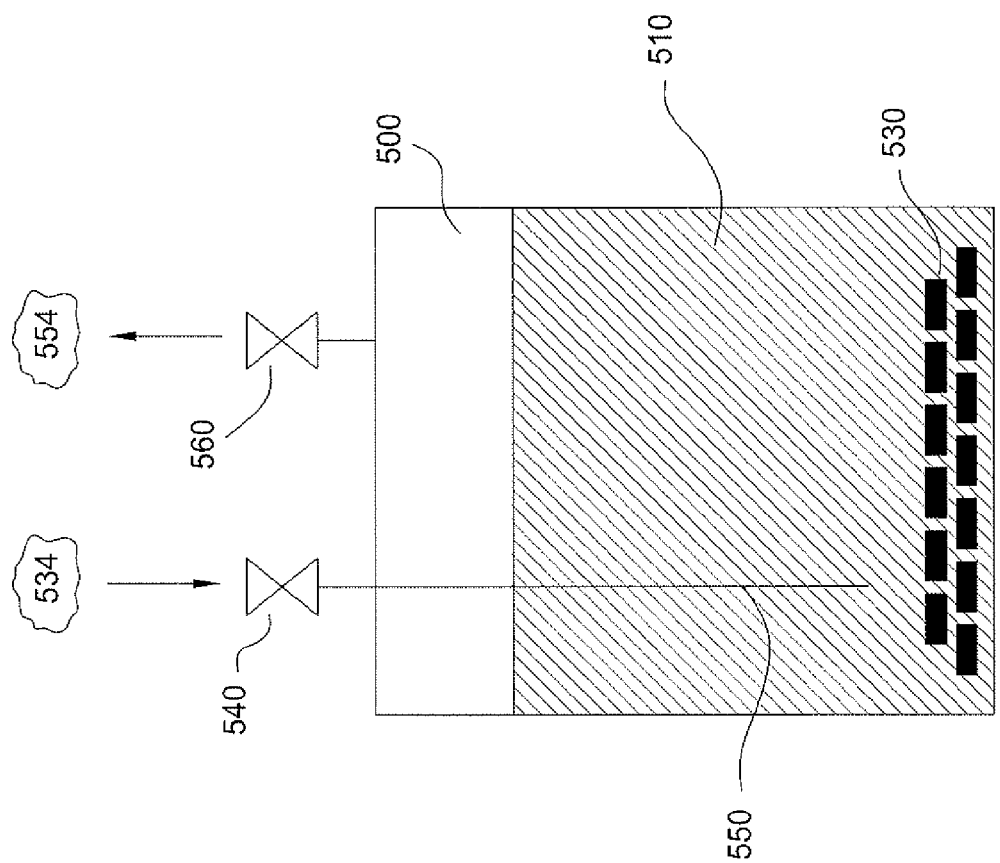
FIG. 5 is a diagram of one embodiment of a bubbler for supplying an organometallic compound containing a metal adsorbent according to embodiments described herein.

One exemplary method of using a bubbler 500 to supply an organometallic compound 510 to a manufacturing tool will be described with reference to FIG. 5. FIG. 5 is a diagram of one embodiment of a bubbler 500 containing a metal adsorbent 530 according to embodiments described herein. The bubbler 500 may be used to supply a gaseous organometallic compound to a manufacturing tool by introduction of a carrier gas 534, for example, argon, into the liquid organometallic compound 510 in the bubbler 500.

The carrier gas 534, for example, argon gas, may be introduced and diffused into the liquid organometallic compound 510 in the bubbler 500 through a carrier gas valve 540 and a sparger 550. The carrier gas 534 in the bubbler 500 is saturated with the vapor of the liquid organometallic compound 510 to form a gaseous mixture 554. This gaseous mixture 554 may be supplied to the manufacturing tool through a supply valve 560.

In the previously described prior art methods, the metallic compound generated by decomposition of the liquid organometallic compound is suspended in the liquid organometallic compound. As the bubbling process proceeds, the decomposed metallic compound scatters with the gaseous mixture and travels downstream. The decomposed metallic compound suspended in the gaseous mixture may deposit on the parts of the supply system. The parts may include the supply tube, filters, gas flow controllers and valves. As the metallic compound accumulates on the parts, the parts may malfunction or stop leading to downtime for the system so the parts may be removed and either cleaned or replaced. Further, if the gaseous mixture delivers the metal particles to the manufacturing tool, the metal particles may contaminate the manufacturing tool and adversely affect the any processes performed in the manufacturing tool.

Referring to FIG. 5, the metallic compounds generated in the liquid organometallic compound 510 in the bubbler 500 during supply may be captured by the metal adsorbent 530 positioned in the bubbler 500. As a result, the gaseous mixture 554 supplied to the manufacturing tool by the bubbler is substantially free of metal particle contamination.

After or prior to use, the metal adsorbent 530 may be cleaned using a cleaning solution comprising at least one of a diluted acid solution and pure water. The metal adsorbent 530 may be dried by exposing the metal adsorbent to an inert gas purge to remove moisture and oxygen from the metal adsorbent 530. The inert gas purge may be performed at an elevated temperature prior to introduction of the metal adsorbent 530 into the bubbler 500. After cleaning and drying the, the metal adsorbent 530 is more effective at capturing the decomposed metallic compound and maintaining the purity of the organometallic compound 510.

It should be understood that the method of removing the metal decomposed compound from the organometallic compound in the bubbler during bubbling supply is exemplary and that the methods described herein not limited to the bubbling supply method described herein. Other exemplary organometallic supplying methods to which the metal adsorbent described herein may be used include methods such as a vapor supply method performed by creating a vacuum in the tank, a gas flow supply method by mixing an inert gas such as argon gas with the vapor of the organometallic compound, and a vapor supply method performed by heating the organometallic compound to increase its vapor pressure.

EXAMPLES

In the following non-limiting examples, the disclosed metal adsorbents and methods of using the disclosed metal adsorbents are explained according to specific embodiments. These embodiments are provided to further illustrate the invention. However, the embodiments are not intended to be all inclusive and are not intended to limit the scope of the inventions described herein. Unless stated otherwise all percentages, parts and ratios are by weight. Examples of the invention are numbered while comparative examples which are not examples of the invention are designated alphabetically.

The examples described below were conducted using DEZn as the organometallic compound, a copper net as the metal adsorbent, and zinc as the metal decomposed compound. DEZn is a preferred material for making transparent conductive oxide (TCO) films for photovoltaic cells. DEZn suffers from the same problems as other organometallic compounds, DEZn self-decomposes during storage, transportation and supply, generating Zn particles (e.g., Zn and/or ZnO) which can lead to maintenance issues as well as contaminating films deposited using the DEZn.

The copper net has a lattice mesh size of 400 micron by 400 microns and is available from TO-TOKU Engineering Corporation of Japan under the name Dixon Packing (Cu).

Heating Test:

In actual operation, DEZn is heated to increase its vapor pressure and flow rate so the adsorption experiments for comparative example A and example 1 were conducted at an elevated temperature to simulate such conditions.

Comparative Example A

Heating Test

Figure 6B:
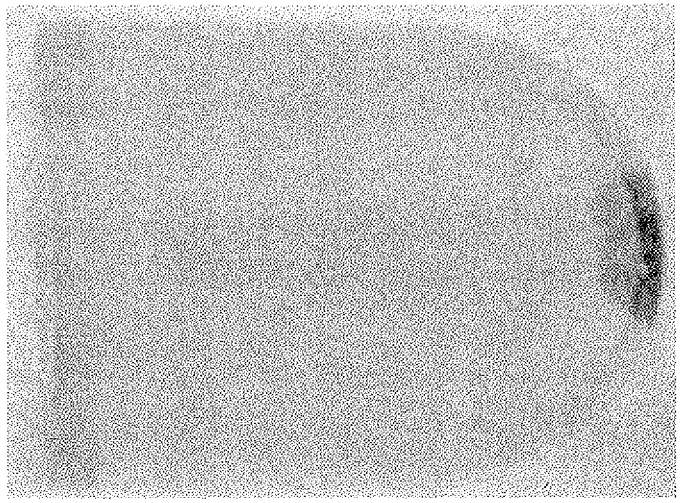
FIG. 6B is a picture of a glass tank containing a DEZn solution without a metal adsorbent according to prior art methods after heating at 80° C. for 2 days.

Prior to introduction of the DEZn into a glass tank (10 mL) the glass tank was vacuumed at 80° C. for a period of six hours to remove oxygen and moisture from the glass tank. The glass tank was filled with liquid DEZn (2.5 mL) and positioned in a glove box in which the dew point was maintained under −50° C. by nitrogen. Zinc particles were generated by heating DEZn at a temperature of 80° C. for a period of two days. As shown in FIG. 6B, when DEZn is heated without a metal adsorbent according to prior art methods, zinc particles were visible within the DEZn solution. The solid zinc residue was rinsed with 1% $HNO_3$.

Example 1

Heating Test

Figure 7A:
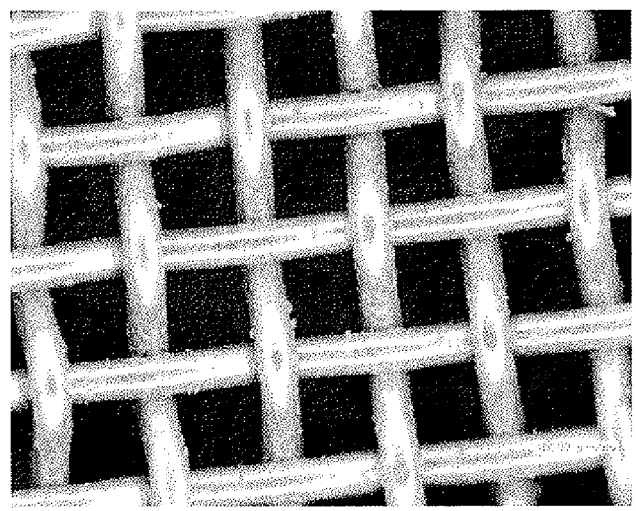
FIG. 7A is a picture of a copper adsorbent prior to exposure to heating and exposure to a DEZn solution.

Prior to introduction of the DEZn into a glass tank (10 mL) with a copper adsorbent positioned therein, both the copper adsorbent and the glass tank were vacuumed at 80° C. for a period of six hours to remove oxygen and moisture from the glass tank and the copper adsorbent. The copper adsorbent was in the form of a net as depicted in FIG. 7A. The glass tank was filled with DEZn in a glove box in which the dew point was maintained under −50° C. by nitrogen flow.

Figure 6A:
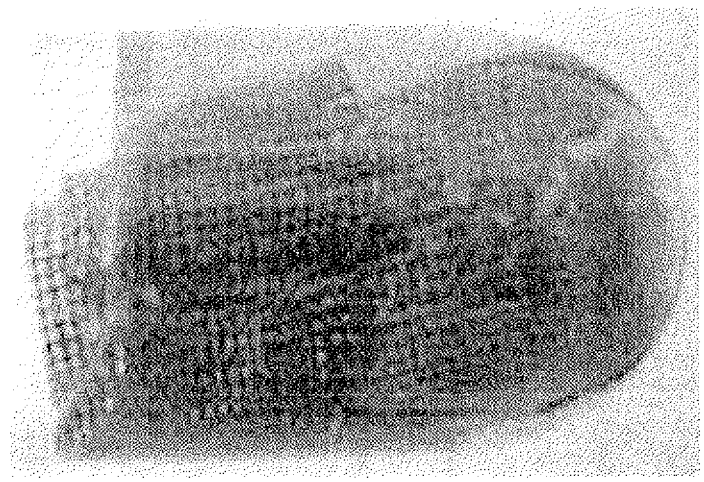
FIG. 6A is a picture of a glass tank containing a DEZn solution and a metal adsorbent according to embodiments described herein after heating at 80° C. for 2 days.

The glass tank (10 mL) with the copper adsorbent was filled with liquid DEZn (2.5 mL). Zinc particles were generated by heating DEZn with the copper adsorbent positioned therein at a temperature of 80° C. for a period of two days. FIG. 6A is a picture of the glass tank after heating a DEZn solution and a metal adsorbent according to Example 1 after heating at 80° C. for two days.

Figure 7B:
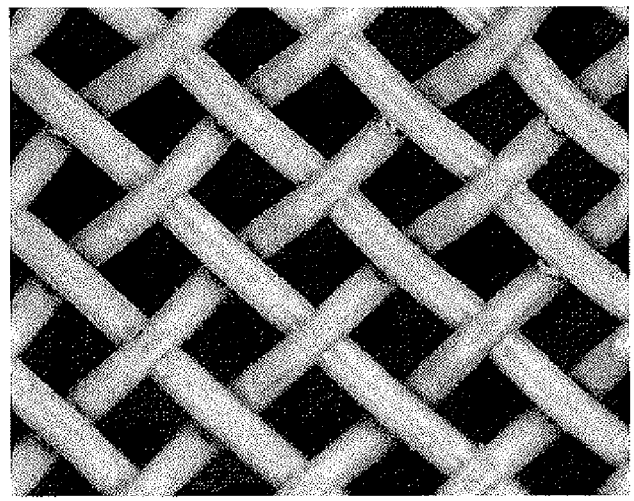
FIG. 7B is a picture of a dried copper adsorbent after two days heating at 80° C. in the presence of a DEZn solution.
Figure 7C:
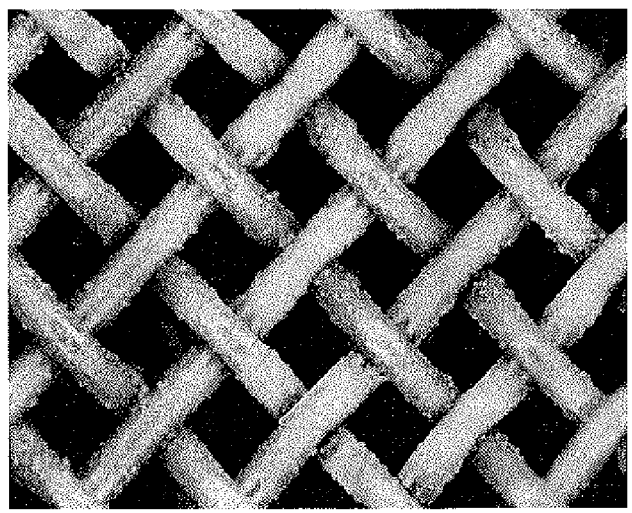
FIG. 7C is a picture of a copper adsorbent after twelve days heating at 80° C. in the presence of a DEZn solution.

After heating the copper adsorbent was extracted from the liquid DEZn solution and both the copper adsorbent and DEZn were dried separately by vacuuming at 60° C. to get solid zinc residue after evaporation of the DEZn. The solid zinc residue was rinsed with 1% $HNO_3$. FIG. 7A is a picture of the copper adsorbent used in Example 1 prior to exposure to heating and exposure to the DEZn solution. FIG. 7B is a picture of the dried copper adsorbent used in Example 1 after two days heating at 80° C. in the presence of the DEZn solution. FIG. 7C is a picture of a copper adsorbent after twelve days heating at 80° C. in the presence of a DEZn solution.

The amount of zinc captured by the copper adsorbent, the amount of zinc remaining in the DEZn, and the ability of the copper adsorbent to capture zinc in the DEZn solution were measured for Comparative Example A and Example 1 and reported in Table I.

TABLE I

|  | Adsorbed Zinc (mg) | Zinc Suspended in the DEZn (mg) | Capturing Ability of the Adsorbent (%) |
|---|---|---|---|
| Comp. Example A | — | 22.2 | — |
| Example 1 | 23.2 | 1.7 | 93 |

As shown in FIG. 6A, the DEZn liquid with the copper adsorbent was very clear by comparison with the liquid of DEZn without the adsorbent as shown in FIG. 6B, where zinc particles were visible in the glass tank. The zinc particles in the glass tank with the adsorbent could not be seen visually.

Referring to FIG. 7A and FIG. 7B, the copper adsorbent having a large surface area captured the zinc particles well after heating. As shown in FIG. 7A, the copper adsorbent had a metallic luster prior to capturing zinc particles, but after heating the copper adsorbent at 80° C. for a period of 2 days in liquid DEZn, the metallic luster of the copper adsorbent was reduced and zinc particles were visible on the surface of the adsorbent as shown in FIG. 7B. As shown in FIG. 7C, the metallic luster of the copper adsorbent is further reduced after twelve days heating at 80° C. in the presence of a DEZn solution.

The amount of zinc remaining in the glass tank was measured by inductively coupled plasma mass spectrometry (ICP-MS). As shown in Table I, 22.2 mg of zinc particles were present in the DEZn after heating without a metal adsorbent at 80° C. for 2 days. However, only 1.7 mg of zinc particles were present in the DEZn (the amount of zinc particles which the adsorbent did not capture) heated with the metal adsorbent under the same conditions. Therefore, the metal adsorbent reduced the diffusion of zinc particles in the DEZn by over 90% even at the elevated temperature of 80° C. Moreover, the zinc particles on the metal adsorbent were strongly attached to the metal surface of the metal adsorbent as the zinc particles would not come off by agitation of the metal adsorbent.

Storage Test:

One purpose of the storage test is to confirm that the metal adsorbent described herein can adsorb the decomposed metallic compound (zinc particles) when DEZn is stored for an extended period of time at room temperature. Another purpose is to demonstrate that clean liquid DEZn without zinc particles may be generated in storage tanks such as the transport tank 300 depicted in FIG. 3 and the storage tank 400 depicted in FIG. 4 using a metal adsorbent to capture the zinc particles.

Comparative Example B

Storage Test

Prior to introduction of the DEZn into a glass tank (10 mL) the glass tank was vacuumed at 80° C. for a period of six hours to remove oxygen and moisture from the glass tank. The glass tank was filled with liquid DEZn (2.5 mL) and stored at room temperature (25° C.) for 60 days to simulate the actual storage temperature.

Example 2

Storage Test

Prior to introduction of the DEZn into a glass tank (10 mL) with a copper adsorbent positioned therein, both the copper adsorbent and the glass tank were vacuumed at 80° C. for a period of six hours to remove oxygen and moisture from the glass tank and the copper adsorbent. The copper adsorbent was in the form of a net as depicted in FIG. 7A. The glass tank was filled with DEZn (2.5 mL) in a glove box in which the dew point was maintained under −50° C. by nitrogen flow.

The glass tank (10 mL) with DEZn and the adsorbent was stored at room temperature (25° C.) for a period of 60 days.

The amount of zinc remaining in the DEZn and the ability of the copper adsorbent to capture zinc in the DEZn solution were measured for Comparative Example B and Example 2 and reported in Table II. The amount of zinc remaining in each glass tank was measured by ICP-MS.

TABLE II

|  | Zinc Suspended in the DEZn (mg) | Capturing Ability of the Adsorbent (%) |
|---|---|---|
| Comp. Example B | ~40 | — |
| Example 2 | ~4 | ~90% |

According to Table II, the amount of zinc particles in the DEZn without the adsorbent was 40 mg/2.5 mL (DEZn); however the amount of zinc particles in the DEZn with adsorbent was only about 4 mg/2.5 mL (DEZn). Therefore the metal adsorbent of this invention reduced the zinc particles suspended in the DEZn by over 90%.

Figure 8B:
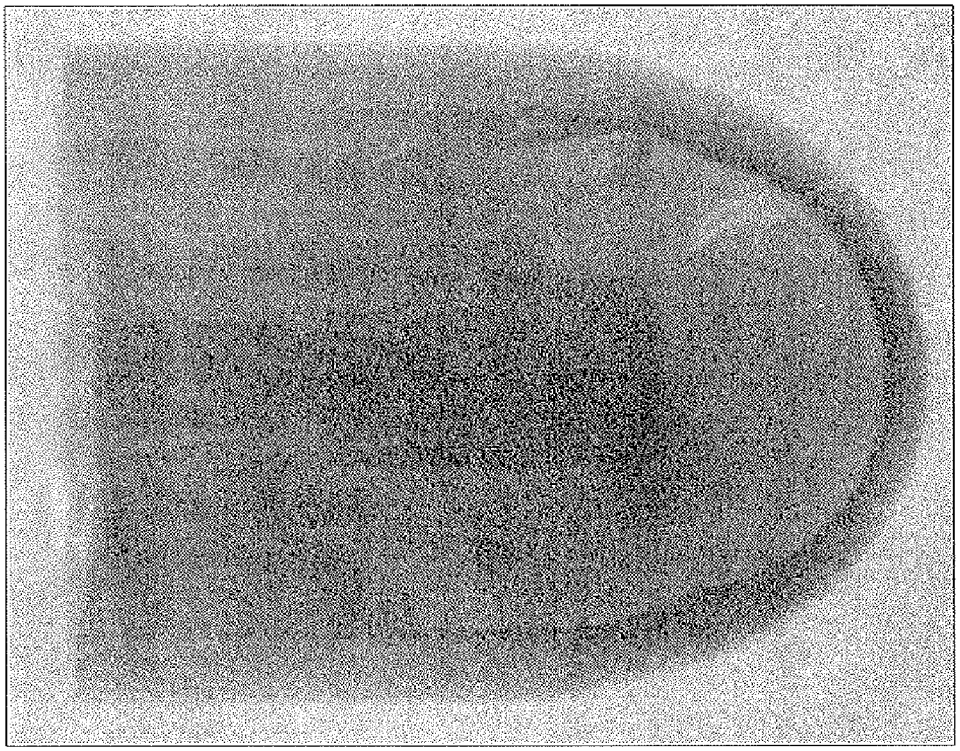
FIG. 8B is a picture of a glass tank containing a DEZn solution without a copper adsorbent after storage at room temperature for a period of time.
Figure 8A:
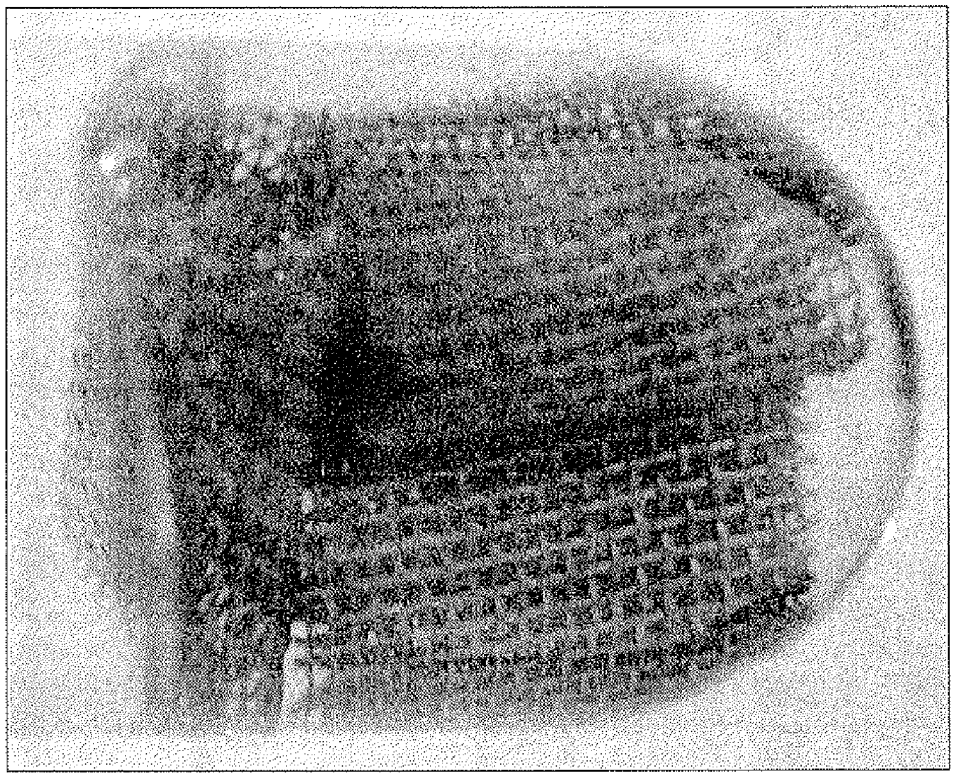
FIG. 8A is a picture of a glass tank containing a DEZn solution with a copper adsorbent after storage at room temperature for a period of time.

FIG. 8A is a picture of the glass tank of Example 2 containing a DEZn solution with a copper adsorbent after storage at 25° C. for a period of 60 days. FIG. 8B is a picture of the glass tank of Comparative Example B containing a DEZn solution without a copper adsorbent after storage at 25° C. for a period of 60 days. As depicted in FIG. 8B, the color of DEZn without the adsorbent was gray because many zinc particles were suspended in the glass tank. On the other hand, as depicted in FIG. 8A, the color of DEZn with the adsorbent was very clear even after 60 days of storage.

Figure 9B:
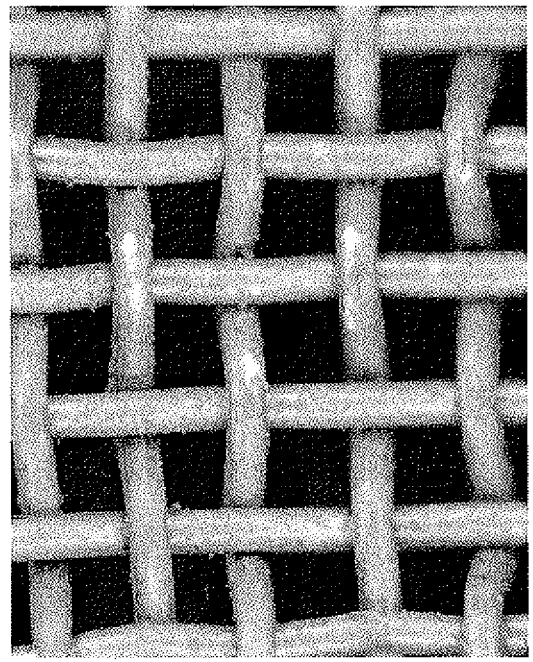
FIG. 9B is a picture of a copper adsorbent after exposure to a DEZn solution.
Figure 9A:
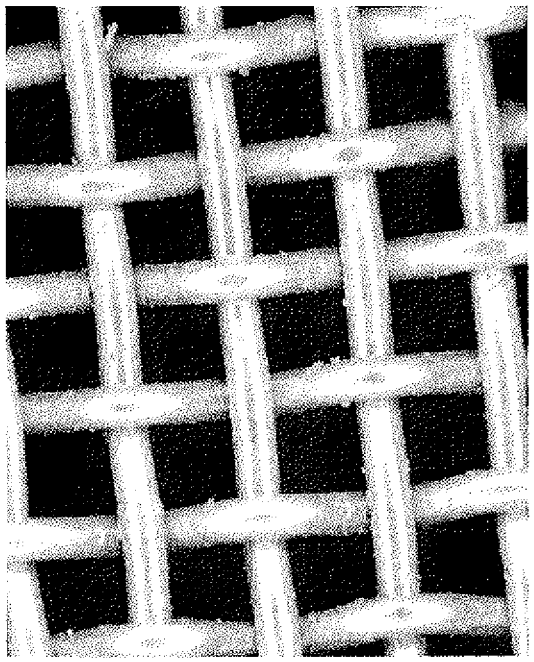
FIG. 9A is a picture of a copper adsorbent prior to exposure to a DEZn solution.

FIG. 9A is a picture of the copper adsorbent of Example 2 prior to exposure to a DEZn solution. FIG. 9B is a picture of the copper adsorbent of Example 2 after exposure to a DEZn solution at room temperature for a period of 60 days. As shown in FIG. 9A, the copper adsorbent had a metallic luster prior to capturing zinc particles, but after exposure to DEZn for a period of 60 days, the metallic luster of the copper adsorbent was reduced and zinc particles were visible on the surface of the adsorbent as shown in FIG. 9B.

As demonstrated by Example 2, the metal adsorbent disclosed herein can significantly reduce zinc particles in DEZn when the DEZn is stored in a tank for an extended period of time during transportation and storage. Further, DEZn stored in the glass tank used in the above experiments is more easily decomposed by comparison with DEZn stored in a storage tank made of stainless steel 316L EP grade, which is typically used, because more moisture and oxygen is typically present on the surface of a glass tank than the surface of a stainless steel tank.

It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present invention is not intended to be limited to the specific embodiments in the examples given above and/or the attached drawings.

While embodiments of this invention have been shown and described, modifications thereof can be made by one skilled in the art without departing from the spirit or teaching of this invention. The embodiments described herein are exemplary only and not limiting. Many variations and modifications of the composition and method are possible and within the scope of the invention. Accordingly the scope of protection is not limited to the embodiments described herein, but is only limited by the claims which follow, the scope of which shall include all equivalents of the subject matter of the claims.

What is claimed is:

1. A method for removing metallic compounds generated from the decomposition of an organometallic compound during the storage, transportation, and supply of the organometallic compound, comprising:
   contacting an organometallic compound that generates a metallic compound from decomposition of the organometallic compound with a metal adsorbent made of metal, wherein at least a portion of the metallic compound is removed from the liquid organometallic compound by the metal adsorbent.

2. The method of claim 1, wherein the organometallic compound and metal adsorbent is positioned in a tank or tube.

3. The method of claim 2, further comprising supplying liquid or vapor of the organometallic compound from the tank or tube.

4. The method of claim 1, wherein the metal of the metal adsorbent is selected from the group consisting of Li, Be, Na, Mg, Al, K, Ca, Sc, Ti, Cr, Mn, Co, Ni, Zn, Ga, Ge, Rb, Sr, Y, Zr, Nb, Mo, Ru, Rh, Pd, Ag, Cd, In, Sn, Sb, Cs, Ba, Hf, Ta, W, Re, Os, Ir, Pt, Au, TI, Pb, Bi, Cu, alloys thereof, and stainless steel.

5. The method of claim 1, wherein the organometallic compound is represented by the formula R-M where R is an alkyl group and M is a metal selected from the group consisting of Li, Be, Na, Mg, Al, K, Ca, Sc, Ti, Cr, Mn, Co, Ni, Zn, Ga, Ge, Rb, Sr, Y, Zr, Nb, Mo, Ru, Rh, Pd, Ag, Cd, In, Sn, Sb, Cs, Ba, Hf, Ta, W, Re, Os, Ir, Pt, Au, TI, Pb, Bi or compound of these metals.

6. The method of claim 1, wherein the organometallic compound is selected from the group consisting of diethyl zinc, dimethyl zinc, triethyl zinc, triethyl aluminum, trimethyl aluminum, trimethyl indium, triethyl indium, trimethyl gallium, or triethyl gallium.

7. The method of claim 5, wherein the metallic compounds removed by the metal adsorbent are M, oxides of M, hydroxides of M, or combinations thereof.

8. The method of claim 1, wherein the metal of the metal adsorbent is copper, the metallic compound is zinc generated by the decomposition of diethyl zinc (DEZn).

9. The method of claim 1, wherein the shape of the metal adsorbent is selected from a plate, a powder, a wire, a net, and combinations thereof.

10. The method of claim 1, wherein the metal adsorbent comprises a copper net.

* * * * *